(12) United States Patent
Fölling

(10) Patent No.: US 9,389,404 B2
(45) Date of Patent: Jul. 12, 2016

(54) METHOD AND LIGHT MICROSCOPY APPARATUS FOR PRODUCING AN IMAGE OF A SAMPLE

(75) Inventor: Jonas Fölling, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 754 days.

(21) Appl. No.: 13/524,458

(22) Filed: Jun. 15, 2012

(65) Prior Publication Data

US 2012/0327209 A1    Dec. 27, 2012

(30) Foreign Application Priority Data

Jun. 22, 2011    (DE) .......................... 10 2011 051 278

(51) Int. Cl.
| | | |
|---|---|---|
| *H04N 7/18* | (2006.01) | |
| *G02B 21/16* | (2006.01) | |
| *G02B 21/36* | (2006.01) | |
| *G01N 21/64* | (2006.01) | |

(52) U.S. Cl.
CPC .............. *G02B 21/16* (2013.01); *G02B 21/367* (2013.01); *G01N 21/6458* (2013.01)

(58) Field of Classification Search
CPC .................................................. G01N 21/6428
USPC ............................................. 348/79; 356/36
IPC ....................................................... G01N 21/64
See application file for complete search history.

(56) References Cited

U.S. PATENT DOCUMENTS

| | | | |
|---|---|---|---|
| 7,675,045 B1 | 3/2010 | Werner et al. | |
| 2006/0028716 A1* | 2/2006 | Gilbert ........................... | 359/368 |
| 2008/0068588 A1* | 3/2008 | Hess et al. ....................... | 356/36 |

(Continued)

FOREIGN PATENT DOCUMENTS

| | | |
|---|---|---|
| DE | 102 46 274 A1 | 4/2004 |
| DE | 103 61 327 A1 | 7/2005 |
| DE | 102004057451 A1 | 6/2006 |

(Continued)

OTHER PUBLICATIONS

M.J. Rust, M. Bates, X. Zhuang, "Sub-diffraction-limit imaging by stochastic optical reconstruction microscopy (STORM)", Nature Methods 3, 793-796 (2006).

(Continued)

*Primary Examiner* — Yulin Sun
(74) *Attorney, Agent, or Firm* — Patentbar International, P.C.

(57) ABSTRACT

A sequence of individual images is acquired by imaging the sample through imaging optics onto an image sensor. For the acquisition of each individual image, the sample is provided with a marker pattern, in which individual markers can be imaged in the form of spatially separable light distributions through the imaging onto the image sensor. The centroid positions of the light distributions are determined and superimposed to form a complete image of the sample. According to the present invention, an image-drift-inducing temperature value ($\Delta T1, \Delta T2, \ldots, \Delta Tn$) is measured during the acquisition of the sequence of individual images. A temperature-dependent drift value ($\Delta X1, \Delta X2, \ldots, \Delta Xn; \Delta Y1, \Delta Y2, \ldots, \Delta Yn$) is correlated to the image-drift-inducing temperature value ($\Delta T1, \Delta T2, \ldots, \Delta Tn$) based on predetermined correlation data. The determined centroid positions are corrected based on the drift value ($\Delta X1, \Delta X2, \ldots, \Delta Xn; \Delta Y1, \Delta Y2, \ldots, \Delta Yn$).

5 Claims, 7 Drawing Sheets

(56) References Cited

U.S. PATENT DOCUMENTS

2008/0182336 A1    7/2008    Zhuang et al.
2009/0134342 A1    5/2009    Hell et al.

FOREIGN PATENT DOCUMENTS

| | | |
|---|---|---|
| DE | 10 2006 021 317 B3 | 10/2007 |
| DE | 10 2008 024 568 A1 | 12/2009 |
| WO | 2004/034124 A1 | 4/2004 |
| WO | 2006/127692 A2 | 11/2006 |
| WO | 2007/128434 A1 | 11/2007 |

OTHER PUBLICATIONS

Geisler C., et al., "Resolution of Lambda/10 in fluorescence microscopy using fast single molecule photo-switching", Appl. Phys. A., 88, 223-226 (2007).

* cited by examiner

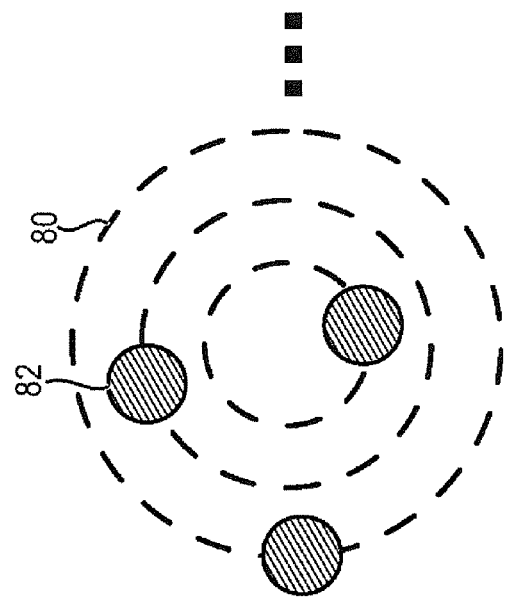
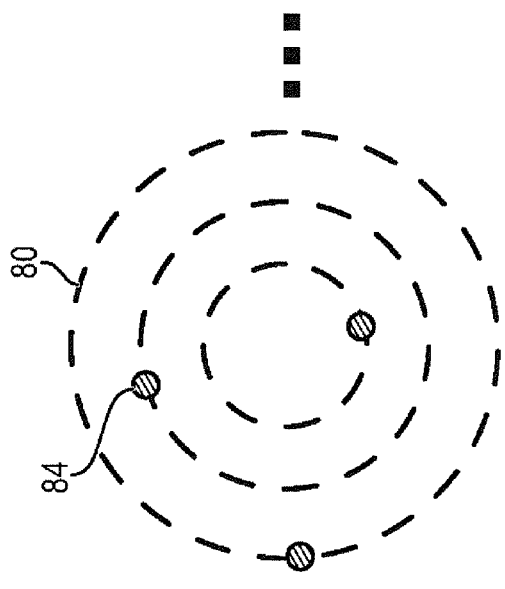
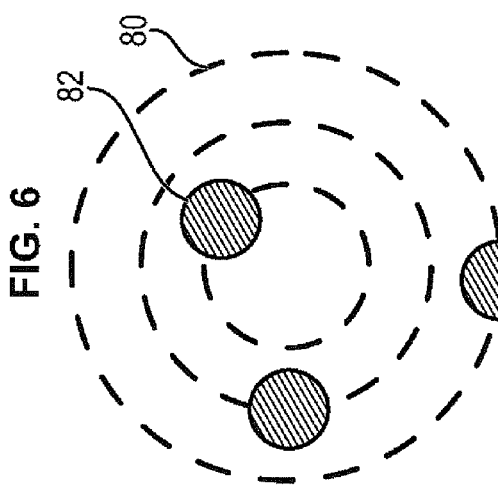
FIG. 6
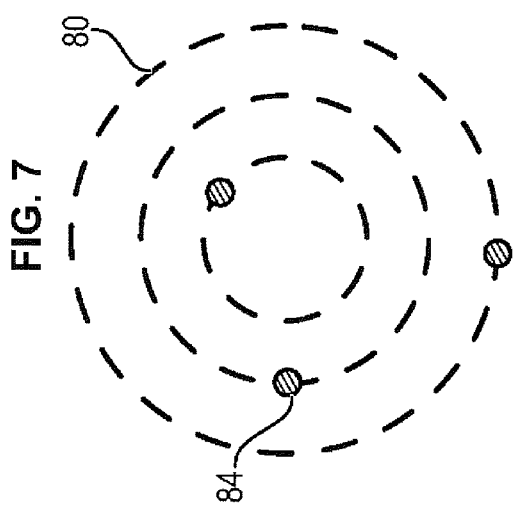
FIG. 7
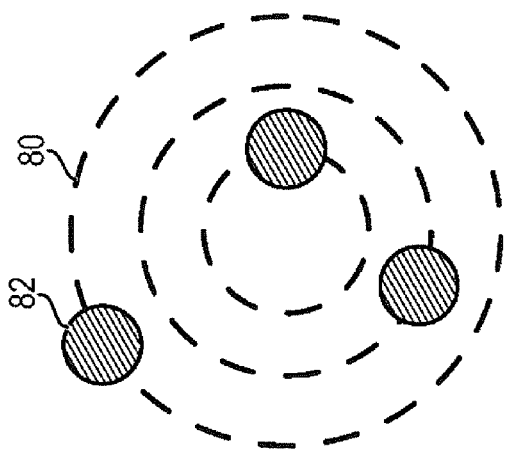
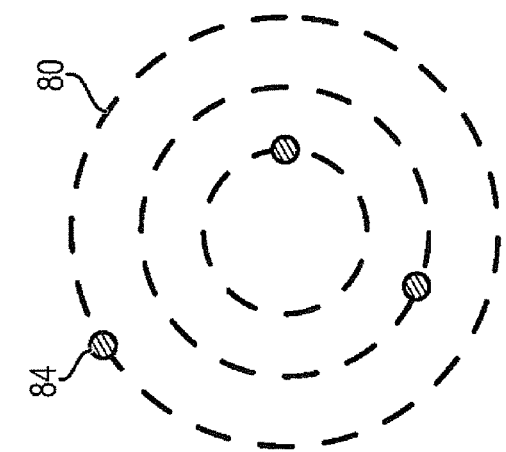

METHOD AND LIGHT MICROSCOPY APPARATUS FOR PRODUCING AN IMAGE OF A SAMPLE

RELATED APPLICATIONS

This application claims priority to German Patent Application No. 10 2011 051 278.0. filed on Jun. 22, 2011, which is incorporated herein by reference in its entirety.

FIELD OF THE INVENTION

The present invention relates to a method for producing an image of a sample using a light microscopy apparatus of the type described in the preamble of claim 1. The present invention further relates to a light microscopy apparatus.

BACKGROUND OF THE INVENTION

In the recent past, light-microscopic imaging methods have been developed with which, based on a sequential, stochastic localization of individual markers, in particular fluorescence molecules, samples can be imaged that are smaller than the diffraction resolution limit of conventional light microscopes. Such methods are described, for example, in WO 2006/127692 A2; DE 10 2006 021 317 B3; WO 2007/128434 A1, U.S. 2009/0134342 A1; DE 10 2008 024 568 A1; "Sub-diffraction-limit imaging by stochastic optical reconstruction microscopy (STORM)", Nature Methods 3, 793-796 (2006), M. J. Rust, M. Bates, X. Zhuang; "Resolution of Lambda/10 in fluorescence microscopy using fast single molecule photo-switching", Geisler C. et al, Appl. Phys. A, 88, 223-226 (2007). This new branch of microscopy is also referred to as localization microscopy. The applied methods are known in the literature, for example, under the designations (F)PALM ((Fluorescence) Photoactivation Localization Microscopy), PALMIRA (PALM with Independently Running Acquisition), GSD(IM) (Ground State Depletion Individual Molecule return) Microscopy) or (F)STORM ((Fluorescence) Stochastic Optical Reconstruction Microscopy).

The new methods have in common that the samples to be imaged are prepared with markers that have two distinguishable states, namely a "bright" state and a "dark" state. When, for example, fluorescent dyes are used as markers, then the bright state is a state in which they are able to fluoresce and the dark state is a state in which they are not able to fluoresce. In order to image a sample with a resolution that is higher than the conventional resolution limit of the imaging optics, a small subset of the markers is repeatedly switched to the bright state. This "active" subset forms a marker pattern whose individual markers, which have been switched to the bright state, have an average distance from each other greater than the resolution limit of the imaging optics. The respective marker pattern is then imaged onto a spatially resolving image sensor which captures the individual markers in the form of spatially separable light distributions.

In this way, a plurality of individual images are captured, in each of which a different marker pattern is depicted. In an image analysis process, then in each individual image, the positions of the centroids of the light distributions are determined, which represent the markers that are in their bright state. The centroid positions of the light distributions determined from the individual raw data images are then combined into one representation in the form a complete image. The high-resolution complete image produced by this combined representation reflects the distribution of the markers.

In order to obtain a representative image of the sample to be imaged, a sufficient number of marker signals must be detected. However, since the number of markers in the particular active marker pattern is limited by the average minimum distance by which two markers in the bright state must spaced from each other, it is necessary to capture a very large number of individual images in order to produce a complete image of the sample. Typically, the number of individual images is in a range from 10,000 to 100,000.

The time required to capture an individual image cannot be less than a lower limit determined by the maximum image acquisition rate of the image sensor. This results in relatively long total imaging times for a sequence of individual images needed for a complete image. The total imaging time may, for example, be up to several hours.

During a total imaging time of such a length, thermal effects, such as thermal expansion, contraction or strain of the mechanical components of the light microscope may result in a drift of the sample to be imaged relative to the imaging optics. Since in order to create a complete high-resolution image, all individual images are combined after the determination of the centroids, any relative movement between the sample and the imaging optics that may occur between the acquisition of two successive individual images will degrade the spatial resolution of the complete image.

SUMMARY OF THE INVENTION

In the following, the problem described above is illustrated with reference to FIGS. 1 through 4.

FIG. 1 is a simplified view of a conventional inverted light microscope 10. Light microscope 10 includes a stand 12, on which a sample stage 14 rests. A sample 16 to be imaged is positioned on a sample holder 15 attached to sample stage 14.

Sample 16 is illuminated by a light source 17 located above sample stage 14. Light source 17 is mounted on a swivel arm 18. Also mounted on swivel arm 18 is a holder 20 carrying various optical systems (not shown in FIG. 1), which are used to implement different illumination modes such as, for example, standard transmitted illumination, or phase contrast illumination. To this end, the optical system provided for the respective illumination mode is rotated in holder 20 into the illumination beam indicated in FIG. 1 by reference numeral 22. The illuminating light emitted by light source 17 is directed onto sample 16 through a condenser 23 attached to the underside of holder 20. To facilitate handling of sample 16, swivel arm 18 can be swung away from sample stage 14 together with the optical systems mentioned above.

A motorized objective turret 24 carrying a plurality of objectives 26 is located below sample stage 14. By rotating objective turret 24 about the optical axis designated O in FIG. 10, objectives 26 can be rotated into the imaging beam path defined by optical axis O. Objective 26, which is currently located in the imaging beam path, images sample 16 onto an image sensor 28 through an opening 19 formed in sample stage 14. Image sensor 28 is connected to a sensor driver 29, which controls image sensor 28. In addition, sensor driver 29 converts sensor signals received from image sensor 28 into image signals for further image processing.

Microscope stand 12 is coupled to a control unit 30, for example, a computer, which can be used to control the functions of the microscope, in particular the image processing. To this end, control unit 30 receives the image signals generated by sensor driver 29. Control unit 30 is connected to a monitor 32, on which is displayed a sample image generated based on the processed image signals. In addition, the sample image may also be viewed through eyepieces 34.

In light microscope 10 shown in FIG. 1, objective turret 24 is mounted to U-shaped stand 12, so that the image-drift-relevant distance between the imaging objective 26 and sample 16 is relatively large. Specifically, sample 16 is coupled with objective 26 via sample holder 15, sample stage 14, U-shaped stand 12, and objective turret 24. This relatively large distance makes the light microscope 10 of FIG. 1 in particular susceptible to thermal instabilities, which, as it were, add up over the distance. Such thermal instabilities may be due to temperature variations in the ambient air or in light microscope 10 itself, which may be caused, for example, by electronic components heating up. As a result of such temperature variations, for example, metallic components holding sample 16 and objective 26 in position change in size due to thermal expansion or contraction, which may cause relative movement between sample 16 and objective 26.

The following estimate illustrates how critical such thermal instabilities may be in high-resolution localization microscopy, where the resolutions achieved are often below 20 nm. Aluminum is a material typically used in the manufacture of metallic microscope components and has a thermal expansion coefficient of 23 ? 10-6 K−1. Assuming, for example, that in light microscope 10 shown in FIG. 1, the image-drift-relevant distance over which sample 16 is coupled with objective 26 is 10 cm, and that this distance is along a path through microscope components made of aluminum, then the resulting mechanical drift is 2.3 μm per 1 K change in temperature. When relating this change in temperature to the spatial resolution mentioned above, it is immediately apparent that temperature variations can have a significant detrimental effect on the quality of the recording.

In light microscope 10 shown in FIG. 1, drift-inducing heat sources are present, for example, in sensor driver 29, which is composed of electronic components and causes stand 12 to heat up. The same applies to motorized components, such as those used to rotate objective turret 24. Moreover, light source 17 as well as mechanical actuators contained in holder 20 also generate heat which may detrimentally affect the imaging accuracy.

In order to prevent thermally induced drift, WO 2004/034124 A1 proposes to mount temperature sensors on a light microscope to measure temperature variations. Based on these temperature variations, control variables are determined, which are used to control motors to move the sample stage in a drift-compensating manner during the imaging of the sample. This closed-loop position control of the stage during image acquisition is technically relatively complex.

It is an object of the present invention to improve a method and a light microscopy apparatus for producing an image of a sample of the type mentioned at the outset in such a way that drift-induced imaging inaccuracies can be reliably avoided in a simple way.

In accordance with the present invention, this object is achieved for the method by the features of claim 1, and for the apparatus by the features of claim 4. Advantageous further embodiments are described in the respective dependent claims.

According to the present invention, an image-drift-inducing temperature value is measured during the acquisition of the sequence of individual images. Based on predetermined correlation data, the image-drift-inducing temperature value is correlated to a temperature-dependent drift value. Finally, the centroid positions determined from the light distributions produced on the image sensor are corrected based on the drift value. These corrected centroid positions can then be superimposed to form a drift-free complete image of the sample.

The present invention takes advantage of the fact that in the method used, the relevant image information that is used for producing an image of the sample is not contained in the raw data collected during the acquisition of the respective individual images itself, but in the centroid positions obtained from this raw data (usually after the actual measurement). These centroid positions are determined from the light distributions produced on the image sensor. This makes it possible to perform the drift correction later; i.e., after acquiring the raw data representing the individual images. This is much easier than, for example, shifting the individual images themselves later based on the determined drift values, because this would require a considerable amount of image processing.

Thus, using the present invention, it is possible to allow drift motion during the actual measurement and to correct for it at a later time using the centroid positions obtained from the raw data. To this end, the image-drift-inducing temperature value is recorded and saved during the measurement; i.e. during the acquisition of the individual images. This may be done continuously or at predetermined intervals. What is essential is that the temperature value is recorded during image acquisition in such a way that later; i.e., after the actual measurement, it can be correlated with the respective individual images, and thus with the centroid positions obtained from these individual images. The temperature-dependent drift value to be used as the basis for the drift correction can then be determined from the temperature value recorded during the measurement.

The present invention is based, inter alia, on the realization that temperature-induced drift motions in the components of the light microscope are typically highly reproducible. Depending on the specific geometric conditions present and the materials used for manufacturing the light microscope, the microscope components frequently move in a predictable manner under the influence of temperature variation. This applies with respect to both the magnitude and the direction of motion. The knowledge of this reproducible behavior is used in accordance with the present invention to provide correlation data which correlate the temperature value with the temperature-dependent drift value. Based on this correlation data, the temperature value measured during the acquisition of the individual images can then be correlated with the corresponding temperature-dependent drift value to be used to correct the determined centroid positions after the image acquisition.

Preferably, the correlation data is experimentally determined and stored in the light microscopy apparatus. It is expedient, for example, to perform a series of measurements once prior to the actual image acquisition. During this test series, the drift value is determined as a function of temperature value and then stored, for example, in the form of a table, a calibration curve, or the like. Preferably, the correlation data is determined only once, e.g., prior to delivering the apparatus to the customer, and is later available for determining the drift value.

Preferably, in order to experimentally determine the correlation data, a reference pattern including at least one reference marker is provided. Then, the image-drift-inducing temperature value is set to a plurality of reference temperature values. An individual reference image of the reference pattern is captured for each reference temperature value, the imaging optics imaging the reference marker of the respective reference pattern in the form of a reference light distribution onto the image sensor. Subsequently, a reference centroid position of the corresponding reference light distribution is determined for each reference temperature value. Finally, the temperature-dependent drift value is determined from the change in the reference centroid positions as a function of the reference temperature values. Thus, in this advantageous embodiment, the correlation data is determined using a method which is substantially the same as the method according to which the light microscopy apparatus is later operated to perform the actual image acquisition. This ensures that the drift value stored in the correlation data accurately reflects the expected image drift.

Preferably, the temperature of at least one component of the light microscopy apparatus is measured as an image-drift-inducing temperature value. Alternatively or additionally, it is possible to measure the ambient temperature as a temperature value. However, measuring the temperature directly on the light microscopy apparatus is likely to allow the conditions that influence the image drift to be determined more accurately.

In an advantageous embodiment, the temperature is measured in or on a sample stage and/or in or on a holding device provided for the imaging optics and/or in or on a stand, on which the sample stage rests. All of the aforementioned components are indirectly or directly coupled with the sample to be imaged or with the imaging optics. Therefore, thermally induced motion of these components significantly degrades the imaging capability of light microscopy apparatus. Thus, by measuring the temperature of such a component during the measurement and subsequently correcting the centroid positions as a function of the measured temperature, thermally induced image shift can be particularly reliably compensated for. In this connection, the temperature can be measured at the surface and/or inside of the respective component. For example, it is advantageous to measure the temperature at a location where there is a heat source which may cause image-drift-relevant temperature variations in or on the light microscopy apparatus. Locations to be considered are in particular those where a motor drive is located.

In a preferred embodiment, the measured temperature value is modified by an inertia compensation value, and the drift value is determined based on the modified temperature value. This embodiment is advantageous in particular when the temperature is measured only at the surface of the respective component. This accounts for the fact that a temperature measured at the surface of a component does often not reflect with sufficient accuracy the image-drift-relevant temperature response of the component itself, in particular its inertia. For example, it is conceivable that a substantially thermally uninsulated temperature sensor that is mounted on the surface of the component and exposed directly to the ambient air could detect a short temperature variation in the environment of the light microscopy apparatus, which does not translate into a corresponding image drift because of the thermal inertia of the component. Thus, in this embodiment, the thermal inertia of the component is, as it were, simulated later so as to accurately reproduce the thermal response of the component in order to determine a suitable drift value. This in particular allows a light microscopy apparatus already in use to be retrofitted more easily with the present invention because when using the aforedescribed inertia compensation, it can, in certain circumstances, be sufficient to mount a temperature sensor just to the surface of a component that is prone to drift, while nevertheless achieving accurate drift compensation.

Preferably, the inertia compensation value is selected based on the rate of change with time of the measured temperature value. For example, temperature variations of very short duration could be substantially disregarded in the determination of the compensating drift value, for example, through temporal averaging of the measured temperature value, because it is known from experience that such short temperature variations have no effect on image drift.

In an advantageous embodiment of the light microscopy apparatus for carrying out the method according to the present invention, a non-volatile data storage device is provided, in which the correlation data is stored. In this data storage device, the correlation data, which, for example, is experimentally determined before the apparatus is put into service, can be stored and subsequently used during the actual operation of the apparatus.

BRIEF DESCRIPTION OF THE DRAWINGS

The present invention will now be described in greater detail with reference to the drawings, in which:

FIG. 6 is a schematic view of several successive individual images, each showing the respective captured light distributions of the various markers;

FIG. 7 shows the individual images of FIG. 6 after the centroid positions have been determined;

DETAILED DESCRIPTION OF THE PREFERRED EMBODIMENTS

Figure 1:
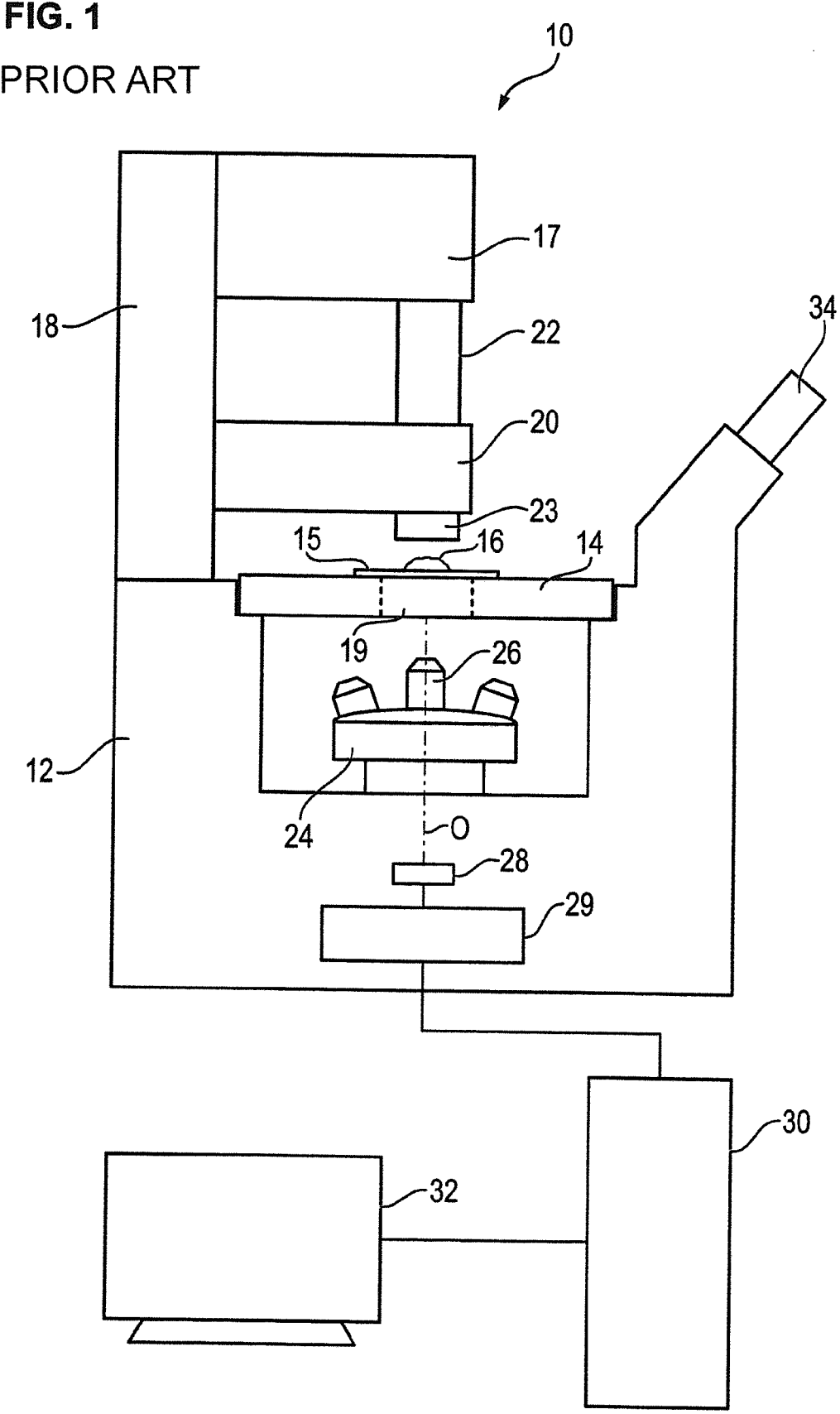
FIG. 1 shows a light microscope according to the prior art.
Figure 2:
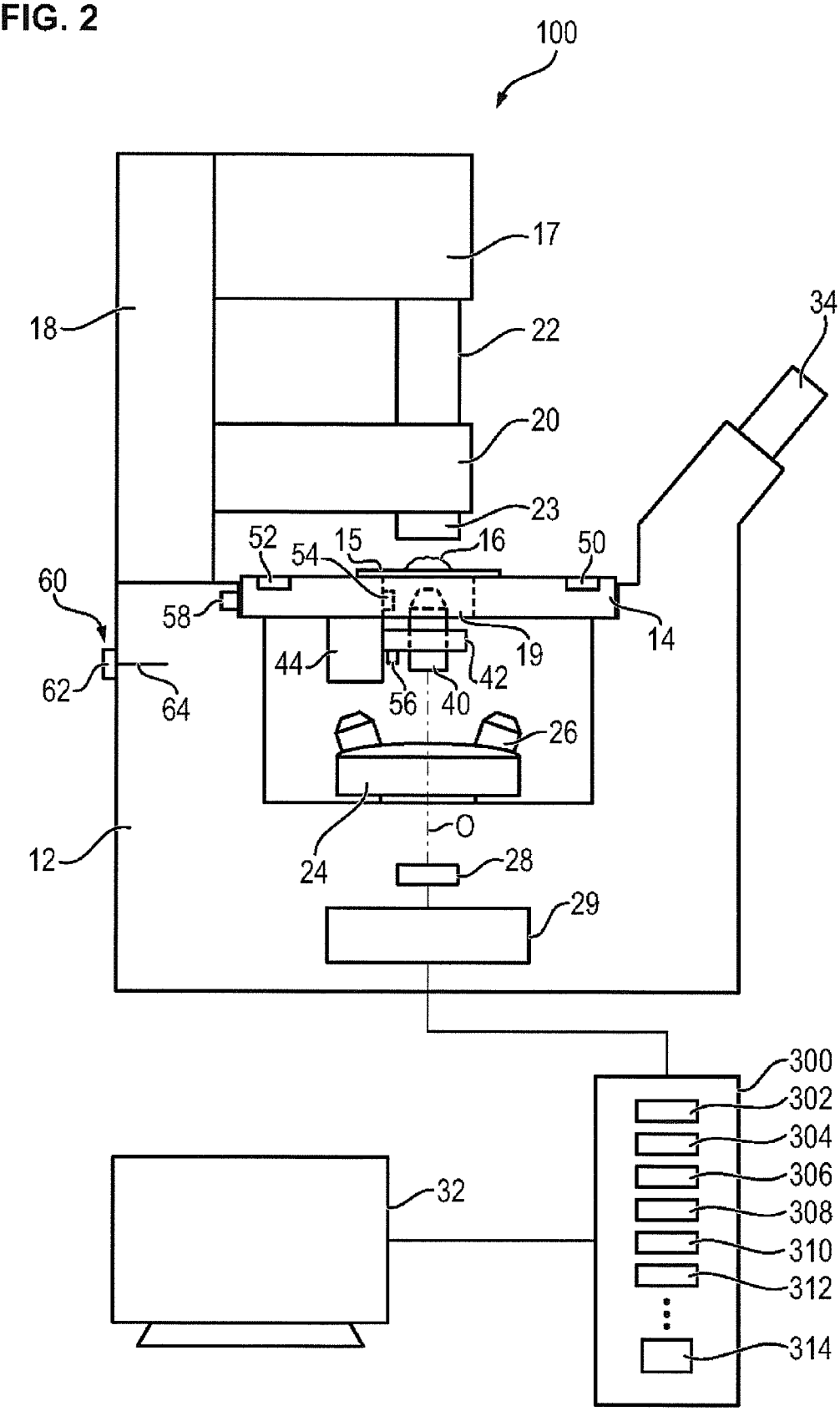
FIG. 2 illustrates an exemplary embodiment of a light microscope according to the present invention.

FIG. 2 shows a light microscope 100 as an exemplary embodiment of the apparatus of the present invention. In the following, only the components and features that distinguish light microscope 100 from the conventional light microscope 10 of FIG. 1 will be described. Components of light microscope 100 which are also present in the conventional apparatus shown in FIG. 1 are indicated by the same reference numerals as in FIG. 1 and will not be described again below.

Light microscope 100 differs from microscope 10 of FIG. 1, first of all, in that a further image-capturing lens 40 is provided in addition to the objective turret 24 carrying objectives 26. Image-capturing lens 40 is supported on a holder 42, which is coupled to a piezoelectric actuator 44 mounted to the underside of sample stage 14. Holder 42 is substantially rotationally symmetric with respect to optical axis O. Piezoelectric actuator 44 is pivotally held to sample stage 14 and enables holder 42, and thus image-capturing lens 40, to be moved along optical axis O in order to focus image-capturing lens 40 on sample 16.

With regard to the image drift expected during image acquisition, the additional image-capturing lens 40 has the advantage over objectives 26 carried on objective turret 24 that it is not coupled via microscope stand 12, but only via the holder 42 and actuator 44 with sample stage 14 on which is located sample holder 15 carrying sample 16. Thus, the distance over which image-capturing lens 40 is coupled with sample 16, is significantly smaller than the distance over which objectives 26 carried on objective turret 24 are coupled with sample 16. In addition, holder 42 also contributes to a reduction of the drift because it is rotationally symmetric with respect to optical axis O, as a result of which, for example, thermal strains acting on image-capturing lens 40 around optical axis O cancel each other out.

However, it should be noted that the inventive solution, which is described in detail below, is not limited to the embodiment shown in FIG. 2, where image-capturing lens 40 is mounted to sample stage 14 via holder 42 and actuator 44. It is also applicable to a conventional configuration, such as is shown, for example, in FIG. 1.

Temperature sensors 50, 52, 54, 56, 58 and 60 are disposed at various locations of light microscope 100. Specifically, temperature sensors 50 and 52 are mounted on the upper side of the stage plate 14 on both sides of opening 19. Temperature sensor 54 is mounted in opening 19 of sample stage 14, while temperature sensor 56 is attached to holder 42. Temperature sensor 58 is mounted in microscope stand 12 at the junction with sample stage 14. Finally, temperature sensor 60 is mounted on the outside of microscope stand 12.

Temperature sensors 50, 52, 54, 56, 58 and 60 may be any kind of device capable of converting temperature into an evaluatable, preferably electrical, quantity. Examples of such devices include those which change their electrical resistance with temperature such as, for example, negative temperature coefficient thermistors, whose resistance decreases with increasing temperature, or positive temperature coefficient thermistors, whose resistance increases with increasing temperature. However, it is also possible to use devices such as semiconductor temperature sensors, which deliver an electrical signal that can be directly processed.

Temperature sensors 50 through 60 are disposed on light microscope 100 at locations where a temperature measurement performed during image acquisition allows a temperature-dependent image drift to be determined in a manner to be described in greater detail hereinafter. In this connection, it should be noted that the arrangement of temperature sensors 50 through 60 shown in FIG. 2 is for illustrative purposes only and in practice will need to be selected according to the actual geometric conditions present and the specific susceptibility of the light microscope to temperature variations. In particular, the susceptibility of the sample stage and of the particular adjustment mechanism of the objective needs to be taken into account in each individual case.

In the exemplary embodiment shown in FIG. 2, temperature sensors 50, 52, 54, 56 and 58 are mounted on, or at least near, the surface of light microscope 100. Specifically, temperature sensors 50 and 52 are provided to measure the temperature at the top surface of sample stage 14, while temperature sensor 54, mounted in opening 19, senses the temperature in the central region of sample stage 14. Temperature sensor 56 senses the temperature at holder 42. Finally, temperature sensor 58 measures the temperature at the junction between heat-generating microscope stand 12 and sample stage 14.

In contrast, temperature sensor 60 is provided to measure the temperature inside of microscope stand 12. Therefore, it has a sensor body 62 mounted on the surface of microscope stand 12 and an adjoining elongated temperature sensing probe 64 inserted into the interior of microscope stand 12 to measure the temperature therein. Again, it should be noted that this arrangement is for illustrative purposes only. For example, a sensor corresponding to temperature sensor 60 could also be mounted on sample stage 14 and/or holder 42. It is also conceivable to provide only a part of temperature sensors 50 through 60, for example, only a single sensor, for measuring image-drift-inducing temperature variations.

Light microscope 100 is connected to a control unit 300, such as a computer. Control unit 300 serves to control the microscope functions and the image processing based on the image signals delivered by sensor driver 29. To this end, control unit 300 includes various processing modules 302, 304, 306, 308, 310 and 312 which, together with temperature sensors 50 through 60, form an image-processing unit, whose operation will be described in greater detail hereinafter. This image-processing unit uses correlation data stored in a non-volatile data storage device 314 provided in control unit 300.

Figure 3:
FIG. 3 is a correlation table on the basis of which temperature values measured during image acquisition are correlated with drift offset values.

In FIG. 3, a data table 400 is shown as an example of the aforementioned correlation data contained in data storage device 314. In data table 400, temperature values $\Delta T1$, $\Delta T2, \ldots, \Delta Tn$ are listed and each is correlated with an X-offset value $\Delta X1, \Delta X2, \ldots, \Delta Xn$ and a Y-offset value $\Delta Y1, \Delta Y2, \ldots, \Delta Yn$. Temperature values $\Delta T1, \Delta T2, \ldots, \Delta Tn$ each indicate a temperature variation with respect to a predetermined reference temperature. Offset values $\Delta X1, \Delta X2, \ldots, \Delta Xn$ and $\Delta Y1, \Delta Y2, \ldots, \Delta Yn$ each indicate a respective offset in the X- respectively Y-direction, by which a centroid position determined from a corresponding light distribution produced on image sensor 28 is shifted as a result of an assumed image drift at the respective temperature variation $\Delta T1$, $\Delta T2, \ldots, \Delta Tn$. In the present exemplary embodiment, the X- and Y-directions are taken to be perpendicular to each other and parallel to the image plane of image-capturing objective 40.

The correlation data specified in data table 400 is experimentally determined and stored in non-volatile data storage device 314 before light microscope 100 is actually put into service. The data is then available when light microscope 100 is put into service and can be used to perform the drift compensation described hereinbelow.

It should be noted that the data table 400 shown in FIG. 3 is for illustrative purposes only. The correlation data could also be provided in any other form, e.g. in the form of a calibration curve. It is also possible to consider not only a two-dimensional offset in the X- and Y-directions, but also a three-dimensional offset, where the respective centroid position is also shifted in a Z-direction along optical axis O.

In the following, an example of how the method of the present invention is carried out will be described with reference to the flow chart of FIG. 4.

After initializing a control variable with the value zero in step S1, the process enters a loop formed by steps S2 through S6, in which, initially, the control variable is increased by one in step S2.

In step 3, a first marker pattern is prepared the first time the aforementioned loop is entered. As described at the outset, such a marker pattern has the feature that only a part of a totality of markers (e.g., fluorescent dyes) is activated; i.e., switched to the bright state. The markers contained in this marker pattern then have an average distance from each other greater than the resolution limit of image-capturing lens 42.

In step S4, the temperature is measured by one of temperature sensors 50 through 60 and stored. In the present exemplary embodiment, functional module 302 contained in image-processing unit 300 is used for storing this temperature.

Subsequently, in step S5, an individual image of sample 16, which has been prepared with the marker pattern, is acquired by imaging sample 16 through image-capturing lens 42 [sic. 40] onto image sensor 28. Sensor driver 29 generates image signals from the sensor signals received from image sensor 28, said image signals being stored in functional module 304, which serves as an image memory.

Step S6, it is queried whether control variable i is less than or equal to a maximum value imax. If this is the case, then the process returns to step S2, so that the aforedescribed steps are performed for the next individual image. However, if control variable i is greater than maximum value imax, then the process continues at step S7.

Once a complete sequence of individual images has been processed according to steps S2 through S6, the individual images are subjected to image processing in step S7. During the image processing performed in step S7, drift compensation is performed, as described further below.

Finally, in step S8, the drift-compensated individual images are superimposed to form a complete image, and the complete image is displayed on monitor 32.

Figure 5:
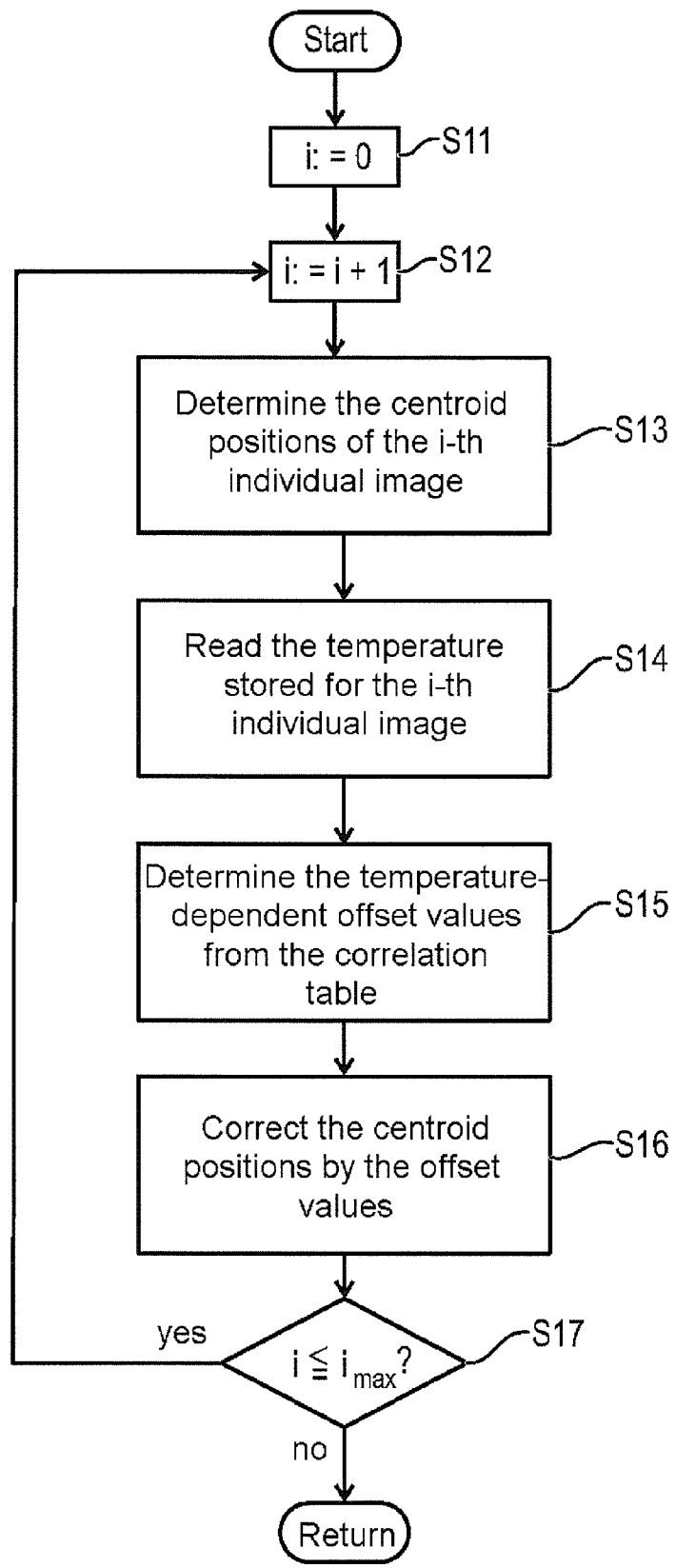
FIG. 5 shows a flow chart of an image processing procedure performed in the method illustrated in FIG. 4.

The flow chart of FIG. 5 exemplifies the image processing performed in step S7.

After initializing control variable i with the value zero in step S11, the process enters a loop formed by steps S12 through S17, which is performed successively for all individual images.

Initially, in step S12, the control variable is increased by one. Then, in step S13, functional module 306 determines the centroid positions of the i-th individual image from the image signals stored in functional module 304. Functional module 306 performs the determination of the centroid positions in a generally known manner by suitably analyzing the light distributions represented by the image signals.

In step S14, functional module 308 reads the temperature value measured and stored in functional module 302 in step S4 for the individual image currently being processed and, in subsequent step S15, it determines from the data table stored in data storage device 314 the offset values in the X- and Y-directions that are correlated with the measured temperature value.

In step S16, functional module 310 corrects the centroid positions using the temperature-dependent offset values determined in step S15. These corrected centroid positions are used later by functional module 312 for displaying the complete image at step S8.

In step S17, it is queried whether control variable i is less than or equal to maximum value imax. If this is the case, then the process returns to step S12 and repeats the drift compensation implemented in steps S13 through S16 for the next individual image. However, if control variable i is greater than maximum value imax, then the drift compensation is complete for all individual images, and the process continues at step S8 of FIG. 4.

Figure 4:
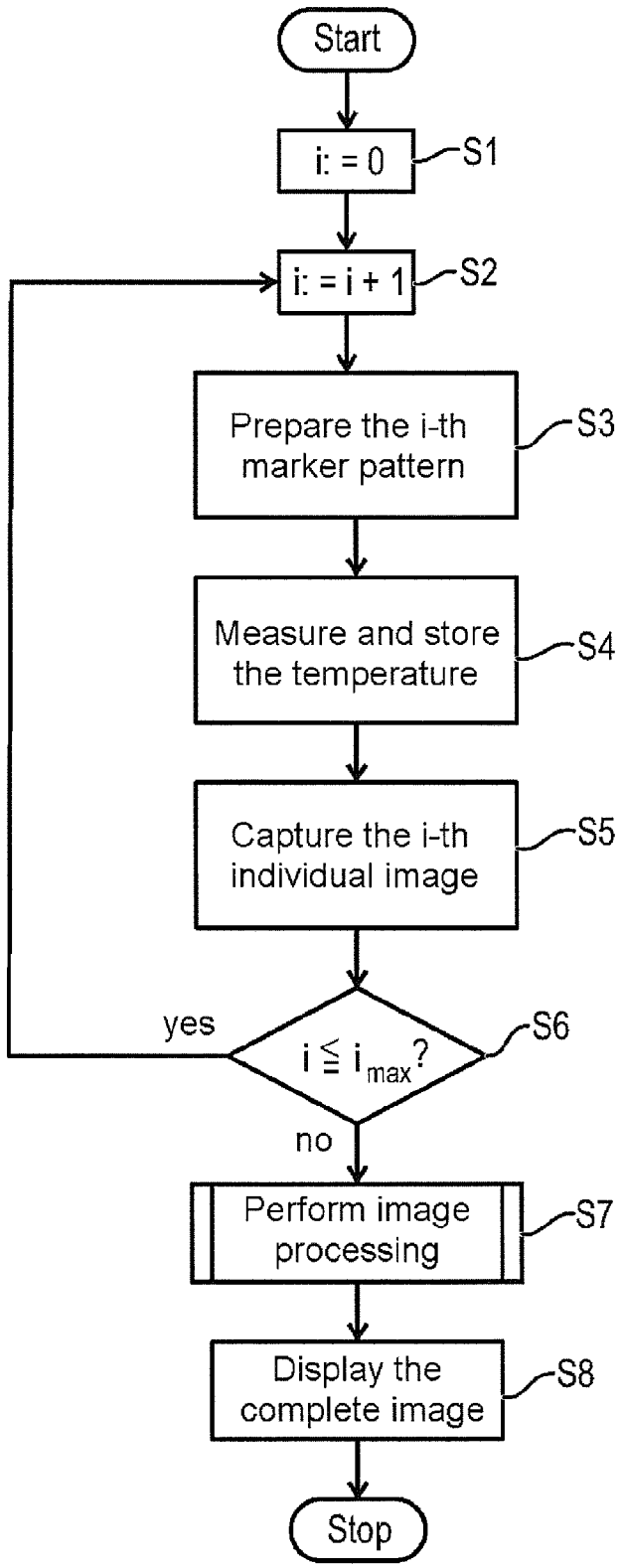
FIG. 4 is a flow chart illustrating an exemplary embodiment of the method of the present invention.

In the exemplary embodiment illustrated in FIGS. 4 and 5, the centroid positions determined for a particular individual image are all corrected by the same temperature-dependent offset values; i.e., only one X-offset value and only one Y-offset value are provided for a particular individual image for a given temperature. However, it is also possible to provide separate temperature-dependent offset values for each centroid position by providing corresponding correlation data. This is advantageous, for example, when the image drift is not uniform over the entire image, but is different at different points in the individual image.

The exemplary embodiment according to FIGS. 4 and 5 illustrates a mode in which, initially, the complete sequence of individual images is captured (steps S2 through step S6) before the individual images are subjected to image processing; i.e., in particular, the centroid positions of the respective individual images are determined and subsequently corrected by the temperature-dependent offset values (step S7, steps S12 through S17). However, it is also possible to perform the image processing, as it were, "on-line"; i.e., to determine the centroid positions and correct them by the temperature-dependent offset values immediately after each of the individual images is captured.

Moreover, in the exemplary embodiment illustrated in FIGS. 4 and 5, the temperature is measured and stored during the acquisition of each individual image (step S4). However, this is not absolutely necessary. Since the temperature generally changes slowly compared to the time required to capture an individual image, it is also possible to measure the temperature at longer intervals and to simply use the last-measured temperature value for the individual images in-between.

The data table shown in FIG. 3 is for the case where only one temperature value is used for drift compensation; i.e., the detection signal of only one of temperature sensors 50 through 60 shown in FIG. 2 is used. However, it is also possible to use a plurality of temperature sensors, and thus a plurality of temperature values for drift compensation, using corresponding correlation data.

FIGS. 6 through 9 once again illustrate how a thermally induced image drift caused by a relative movement between sample 16 to be imaged and image-capturing lens 40 can be counteracted using the method of the present invention. For the sake of simplicity, it is assumed that the sample structure to be imaged is composed of three concentric circles. In FIGS. 6 through 9, these circles are denoted by reference numeral 80.

In FIG. 6 shows, from left to right, successive individual raw data images, each showing a different marker pattern. The active markers appear in the individual raw data images as wide light distributions 82, whose size is determined by the resolution limit of image-capturing lens 40. As can be seen in FIG. 6, light distributions 82 have an average distance from each other greater than this resolution limit determining the size of light distributions 82.

FIG. 7 illustrates how centroid positions 84 of light distributions 82 are determined from the individual raw data images shown in FIG. 6.

Figure 8:
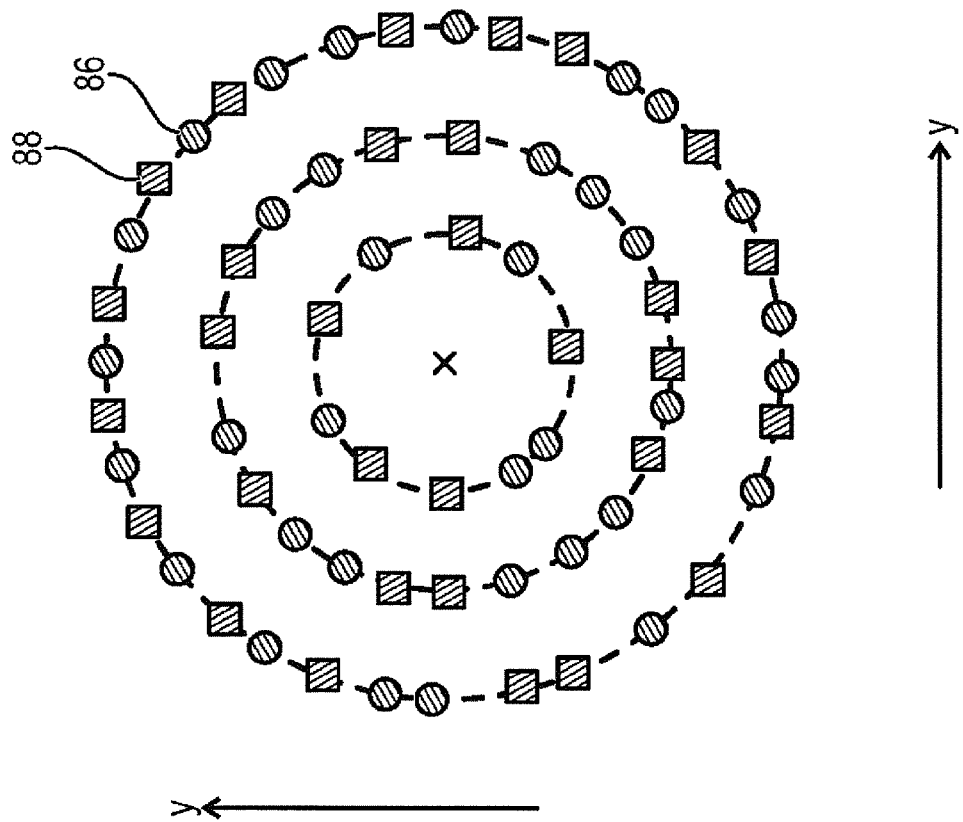
FIG. 8 is a schematic view illustrating the effect produced by an image drift occurring during the acquisition of two individual images.

FIG. 8 illustrates how the spatial resolution of the complete image may be degraded, for example, as a result of relative movement occurring between sample structure 80 to be imaged and image-capturing lens 40 between the acquisition of two successive individual raw data images. In this example, which is for illustrative purposes only, the centroid positions determined from a first individual raw data image are denoted by circles 86, and the centroid positions determined from a second individual raw data image captured later are denoted by squares 88. Further, it is assumed that the temperature measured during the acquisition of the individual raw data images is different for these two individual raw data images.

FIG. 8 illustrates that the thermally induced image drift causes a shift of the second individual raw data image with respect to the first individual raw data image. Therefore, centroid positions 88 derived from the second individual raw data image each have a positional offset, which results in a degradation of the spatial resolution of the complete image composed of the two individual images. In the example of FIG. 8, the positional offset is taken to be ΔX.

Figure 9:
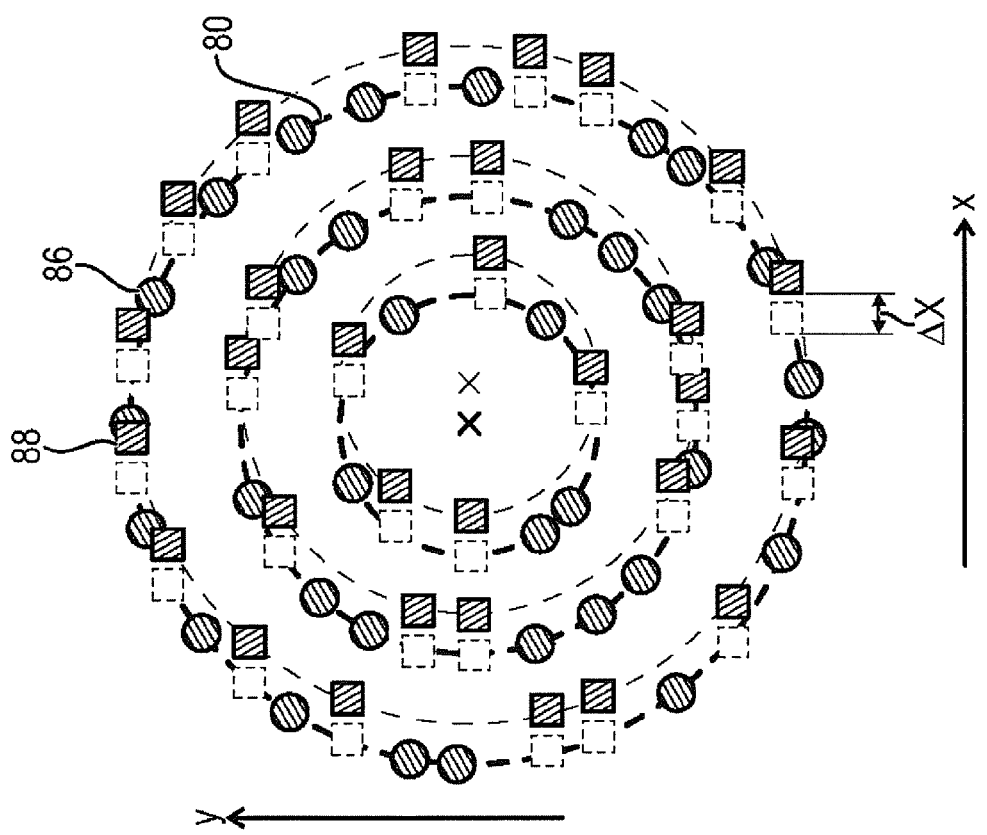
FIG. 9 shows the two individual images of FIG. 8 after the image drift has been compensated for in accordance with the present invention.

FIG. 9 shows the complete image composed of the centroid positions 86 and 88 after the drift compensation. In the present example, the drift compensation according to the present invention consists in that the determined centroid positions 88 according to FIG. 8 are corrected by an offset value based on correlation data (shown, by way of example, in FIG. 3) so as to compensate for positional offset ΔX. As is apparent from FIG. 9, the drift-compensated complete image reflects sample structure 80 with a higher spatial resolution than the complete image without drift compensation.

What is claimed is:

1. A method for producing an image of a sample using a light microscopy apparatus including imaging optics and an image sensor, comprising the following steps:
   acquiring raw data representing a sequence of individual images by sequentially imaging the sample through the imaging optics onto the image sensor;
   the sample being provided, for the acquisition of each individual image, with a marker pattern, in which individual markers can be imaged in the form of spatially separable light distributions through the imaging optics onto the image sensor;
   determining centroid positions of the light distributions, which represent the imaged markers in the respective individual images; and
   superimposing the centroid positions to form a complete image of the sample,
   wherein
   an image-drift-inducing temperature value (ΔT1, ΔT2, . . . , ΔTn) is measured during the acquisition of the raw data representing the sequence of individual images;
   a temperature-dependent drift value (ΔX1, ΔX2, . . . , ΔXn; ΔY1, ΔY2, . . . , ΔYn) is correlated to the image-drift-inducing temperature value (ΔT1, ΔT2, . . . , ΔTn) based on predetermined correlation data; and
   the determined centroid positions are corrected based on the drift value (ΔX1, ΔX2, . . . , ΔXn; ΔY1, ΔY2, . . . , ΔYn), and
   a drift-free said complete localization microscopy image of the sample is formed, based on the corrected centroid positions after acquiring the raw data representing the sequence of individual images.

2. The method as recited in claim 1, wherein a temperature of at least one component of the light microscopy apparatus is measured as an image-drift-inducing temperature value (ΔT1, ΔT2, . . . , ΔTn).

3. The method as recited in claim 2,
   wherein the temperature is measured in or on a sample stage and/or in or on a holding device provided for the imaging optics and/or in or on a stand, on which the sample stage rests.

4. The method of claim 1 wherein the light microscopy apparatus comprises:
   the imaging optics for forming the image of the sample;
   the image sensor for sensing, in a spatially separated manner, the light distributions which are produced by the imaging optics and represent the imaged markers; and
   an image-processing unit including a determination module for determining the centroid positions of the light distributions, which centroid positions represent the imaged markers in the respective individual images, and further including a superposition module for superimposing the determined centroid positions to form the complete image of the sample,
   wherein the image-processing unit further includes:
   at least one temperature sensor for measuring the image-drift-inducing temperature value (ΔT1, ΔT2, . . . , ΔTn) during the acquisition of the raw data representing the sequence of individual images;
   a storage module for storing the measured temperature value (ΔT1, ΔT2, . . . , ΔTn);
   a correlation module for correlating the image-drift-inducing temperature value (ΔT1, ΔT2, . . . , ΔTn) to the temperature-dependent drift value (ΔX1, ΔX2, . . . , ΔXn; ΔY1, ΔY2, . . . , ΔYn) based on the predetermined correlation data; and
   a correction module for correcting the determined centroid positions based on the drift value (ΔX1, ΔX2, . . . , ΔXn; ΔY1, ΔY2, . . . , ΔYn).

5. The method as recited in claim 4,
   wherein the at least one temperature sensor includes a first temperature sensor disposed in or on a sample stage and/or a second temperature sensor disposed in or on a holding device provided for the imaging optics and/or a third temperature sensor disposed in or on a stand, on which the sample stage rests.

* * * * *